United States Patent [19]
Taylor et al.

[11] Patent Number: 6,125,636
[45] Date of Patent: Oct. 3, 2000

[54] THERMO-VOLTAIC PERSONAL COOLING/HEATING DEVICE

[75] Inventors: Charles E. Taylor, Sebastopol; Shek Fai Lau, Foster City, both of Calif.

[73] Assignee: Sharper Image Corporation, San Francisco, Calif.

[21] Appl. No.: 09/231,917

[22] Filed: Jan. 14, 1999

[51] Int. Cl.[7] .................................................. F25B 21/02
[52] U.S. Cl. .............................................. 62/3.5; 62/259.3
[58] Field of Search ....................................... 62/3.5, 259.3

[56] References Cited

U.S. PATENT DOCUMENTS

| | | | |
|---|---|---|---|
| 3,648,469 | 3/1972 | Chapman | 62/3 |
| 4,470,263 | 9/1984 | Lehovec et al. | 62/3 |
| 4,640,284 | 2/1987 | Ruderian | 128/399 |
| 4,930,317 | 6/1990 | Klein | 62/3.3 |
| 5,802,865 | 9/1998 | Strauss | 62/259.3 |
| 5,867,999 | 2/1999 | Bratton et al. | 62/259.3 |
| 5,956,963 | 9/1999 | Lerner | 62/259.3 |
| 5,970,718 | 10/1999 | Arnold | 62/3.5 |

*Primary Examiner*—Henry Bennett
*Assistant Examiner*—Mark Shulman
*Attorney, Agent, or Firm*—Flehr Hohbach Test Albritton & Herbert LLP

[57] ABSTRACT

A self-contained personal cooling and/or heating device includes a heat dissipating member that fits around a portion of the user's body to be thermally regulated. A Peltier thermo-voltaic module operated with low voltage at relatively low current is thermally coupled to the rear surface of the member, and the rear surface of the module is provided with a large surface area, preferably augmented by a heat sink. A fan directs ambient air onto this rear module surface or heat sink. The device preferably is controlled by a microprocessor that biases the module with a pulse train, samples temperature across the module during an off-portion of the pulse train, and used sampled signals to vary duty cycle and/or amplitude of the voltage across the module to finely control temperature. The device preferably is controlled by a self-contained battery source whose polarity across the module is user-changeable, causing the device to heat or cool the user as desired.

20 Claims, 5 Drawing Sheets

THERMO-VOLTAIC PERSONAL COOLING/HEATING DEVICE

FIELD OF THE INVENTION

The present invention relates generally to personal cooling/heating devices, and more particularly to such devices that are self-contained and may be worn around the neck, head or other body portion of a user.

BACKGROUND OF THE INVENTION

Individuals often wish to be cooled, especially in warm ambient temperatures. The desire to be cooled may arise indoors or out, while exercising, engaging in sports, driving, or being in an environment that is not comfortably cool. It may also be desirable to cool a portion of a user's body for medical reasons. Alternatively, in cold environments or perhaps to aid in recovering from an illness or injury, it can be beneficial to heat a portion of an individual's body.

It is known in the art to provide a cap to be worn by an individual that can provide some cooling. U.S. Pat. No. 5,365,607 to Benevento, for example, discloses a cap whose headband includes a plurality of tapered porous pads. The pads are wet with water and apparently produce a cooling effect to the user's head as the water evaporates.

U.S. Pat. No. 3,029,438 to Henschel discloses a water-cooled cap in which an inner aluminum strip contacts the wearer's head, and is contacted with at least one water absorbent sponge strip over-covered by a fabric. The sponge material is moistened and as the water evaporates the aluminum strip cools, thus cooling the wear's head.

Of course other caps may be worn to warm a user. However typically the same cap is not adapted for cooling and for warming the user.

U.S. Pat. No. 4,130,902 to Mackenroth discloses a cooling hat band that includes an outer support band, an inner absorbent band, a wicking element and a water reservoir. Reservoir water moves along the wicking element to the absorbent band, whence it evaporates, passing through holes in the support band. The evaporative effect is said to remove heat from the headband, and thus from the wear's forehead.

However, not all individuals like to wear caps, and participation in some sports, e.g. bicycling, may dictate that another type of headgear be worn, a helmet for example. Thus, several attempts have been made in the prior art to improve upon a basic cooling band, such as a tennis player might wear around the forehead. For example, U.S. Pat. No. 4,742,581 to Rosenthal discloses a laminated cooling band. The band comprises a skin-contacting air pervious heat conductive layer edge-connected to an air pervious fabric that is moistened with water exposed to ambient air. This device is said to cool the wearer as water evaporates from the outer fabric. However, as is typical with many prior art devices, evaporative cooling is dependent upon ambient air motion. If the wearer is stationary, the efficiency of evaporative cooling decreases. Further, Rosenthal's band does not appear to provide an option to heat rather than cool the user.

A substantially new type of personal cooling device is disclosed in U.S. Pat. No. 5,802,865 to Strauss (1998). The Strauss device disposes self-supporting heat sink around the user's neck (or other body portion to be cooled). Body heat is transferred to the heat sink and is actively carried away by fan-induced flow of moistened air. Although the Strauss device works admirably well, it is mechanically complex to fabricate and provides little cooling unless the fan is operating and the device is replenished with liquid. Further, it is difficult to precisely control the extent of cooling. Finally, like many prior art devices, Strauss' device cools but cannot heat.

Figure 1A:
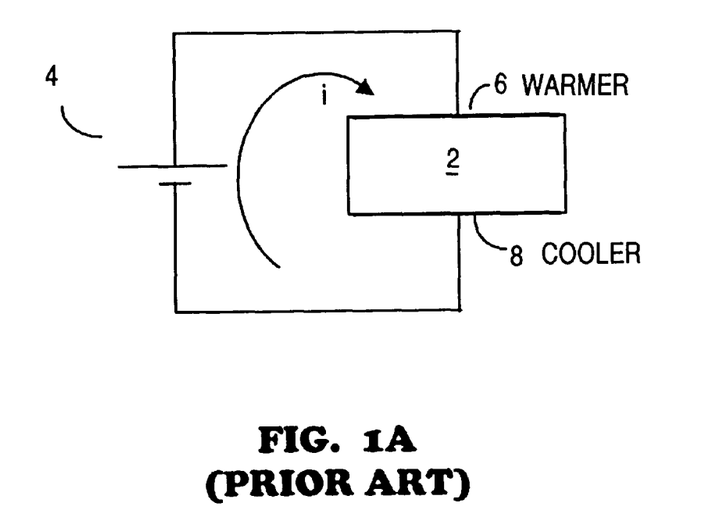
FIGS. 1A and 1B depict heating and cooling with a Peltier thermo-voltaic device, according to the prior art.

A prior art device that is able to heat or cool is shown in FIG. 1A. FIG. 1A depicts a prior art Peltier thermoelectric device 2 coupled to a source of operating potential 4. Device 2 comprises two dissimilar electrical conducting materials (often metals) that form a junction. When device 2 is coupled to power source 4, electrical current "i" flows in the direction shown. Interestingly, the temperature at the device junction rises or falls, relative to ambient temperature, depending upon polarity of i. For example, if the two metals are copper and bismuth, the copper-bismuth junction temperature will increase when positive charge flows from the bismuth to the copper metal. Thus, the bias configuration of FIG. 1A will cause surface 6 of device 2 to be warmer by $\Delta T$ degrees relative to surface 8. If surface 8 is at ambient temperature, perhaps 20° C., then surface 6 will attempt to reach perhaps 23° C.

Figure 1B:
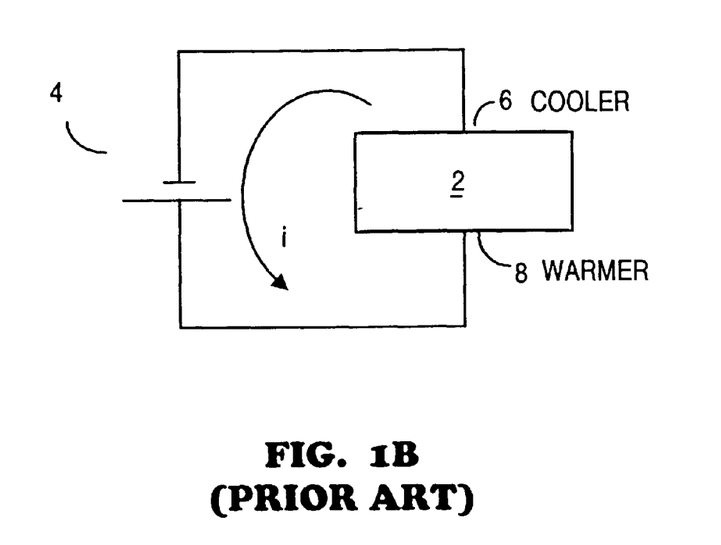

On the other hand, if bias polarity is reversed as shown in FIG. 1B, junction temperature will decrease when the current flow is from the bismuth to the copper metals. Thus, surface 6 will now attempt to be cooler than surface 8 by $\Delta T$.

Conductors other than bismuth and copper may be used. More modern Peltier thermoelectric devices 2 use semiconductor materials, materials that advantageously are good conductors of electricity but poor conductors of heat. Such devices often comprise bismuth telluriude that is heavily doped to create n-type and p-type semiconductor material. A number of such p-type and n-type materials are formed as thermocouple pairs that are sandwiched between ceramic plates and are electrically series-coupled to a power source 4.

Unfortunately even modern Peltier thermo-voltaic devices 2 have not lent themselves to portable or self-contained cooling and/or heating applications because the operating potentials and currents are large. Typically operating potential for source 4 might be 15 VDC, and the magnitude of current i is perhaps 6 A. While an automobile battery could power such devices for a short time, such batteries hardly lend themselves to portability in a personal cooling/heating application. Understandably this range of power consumption has excluded Peltier thermo-voltaic devices from self-contained battery operated applications.

An additional problem with Peltier thermo-voltaic devices is that as soon as the operating potential is removed (e.g., current flow is halted), the thermal effect tends to reverse. Thus in FIG. 1A, if surface 6 of device 2 was intentionally made warmer, turning off or removing the power source 4 would cause surface 6 to become cooler (and surface 8 to try to become warmer). In a personal cooling/heating device application (assuming the problem of provide sufficient operating power were overcome), this reversal effect is most unpleasant. A person trying to warm up with a Peltier thermo-voltaic device must remove the device almost instantly upon turning off the power source to avoid being cooled. Similarly, a person trying to become cooler with such a device could suddenly find themselves being warmed upon turning off the power source.

Thus, there is a need for a self-contained personal device that promotes efficient cooling or heating. If worn about the user's neck, such device should not require headgear. Further, such device should be useable on other portions of the user's body, the forehead, for example. Preferably, such device should be simple to implement mechanically, offer precise temperature control, and be useable for cooling or for heating. Such device should be simple to use and wear, and should provide cooling or heating for several hours without replenishment of the energizing source.

The present invention provides such a device.

SUMMARY OF THE PRESENT INVENTION

The present invention provides a self-contained device that can fit conformably about a user's neck or forehead (or other body portion) to provide cooling or heating, as selected by the user. The device operates dry, that is, without the need for application of any external cooling liquid. The device includes a generally "C-shaped" heat sinking or dissipating member. A user-facing surface of this member is urged against the portion of the user's body to be temperature controlled, and a Peltier thermovoltaic module is attached in good thermal contact to the device-facing surface of this member. The device preferably includes a polarized low voltage battery power source, a fan (e.g., a fan motor and blade assembly), and associated electronic circuitry. The device also provides user-operable controls to regulate temperature at the heat sinking/dissipating member, to select cooling or heating mode of operation, and to select high or low mode operation. Preferably the electronic circuitry should also substantially minimize the reverse heating or cooling effect that is characteristic of Peltier thermo-voltaic devices when the operating power source is interrupted.

When the device is worn, the exposed user-facing surface of the sinking/dissipating member is urged into contact with the body portion to be cooled or heated. The opposite surface (or rear surface) of the member, which is in good thermal contact with the Peltier thermo-voltaic module, preferably defines a larger surface area than the user-facing surface. This rear surface may define heat fins or the like to increase surface area, or a heat sink may be disposed in good thermal contact with the rear surface to improve heat transfer therefrom. An on/off switch couples polarized operating potential of the proper polarity to the Peltier thermo-voltaic module and to the fan. When energized, the thermo-voltaic module seeks to create a temperature differential of about 7° F. (4° C.) between the module surface in thermal contact of the module and ambient air.

In user-selected cooling mode, polarity of the battery or other power source is changed to bias the Peltier thermo-voltaic module such that the module surface in thermal contact with the dissipating member becomes cooler than the opposite module surface. In this mode, the fan cools the other module surface, which promotes further cooling of the dissipating member-facing module surface, and thus of dissipating member and the user. In user-selected heating mode, battery polarity is reversed and resultant module bias is such that the module surface in thermal contact with the dissipating member becomes warmer than the opposite module surface. In this mode, the fan warms the other module surface, which promotes further heating of the dissipating member-facing module surface, and thus of the user.

In contrast to prior art applications, the present invention operates a generic Peltier thermo-voltaic device at low voltage and low current, yet achieves surprisingly efficient operation. Electronic circuitry preferably housed with the present invention monitors the precise extent of heating or cooling achieved and makes compensatory changes as necessary in the power source seen by the module to achieve a user-selected temperature. Further, the electronics also provides an idle mode to minimize the instant reverse thermal effect characteristic of Peltier thermo-voltaic devices when the operating potential is turned off.

The Peltier thermo-voltaic module is driven with a pulse train of voltages that define a module "on time" and an "off time". High or low mode operation is affected by changing duty cycle and/or amplitude of the drive pulses. During the "off time", a feedback circuit senses the voltage intrinsically developed by the Peltier thermovoltaic module. This "no current" intrinsic voltage provides a good measure of the temperature of the module, and thus of the heat dissipating member. A feedback circuit uses the intrinsic voltage to refine control of the drive signal to the module. A user-operable control permits fine tuning of the temperature at the user's body portion.

Other features and advantages of the invention will appear from the following description in which the preferred embodiments have been set forth in detail, in conjunction with the accompanying drawings.

DETAILED DESCRIPTION OF THE PREFERRED EMBODIMENT

Figure 2:
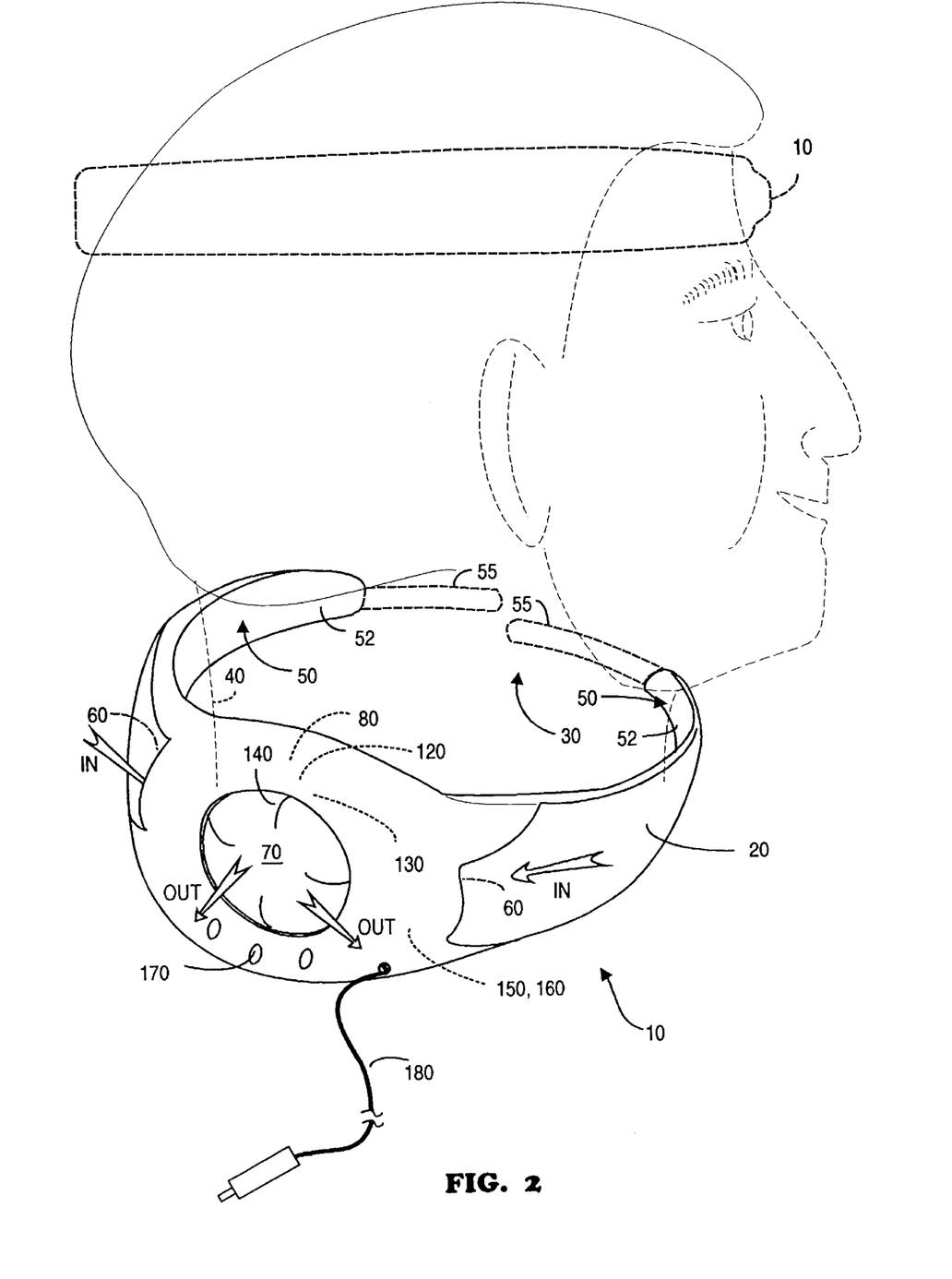
FIG. 2 is a perspective view of the present invention worn by a user.

FIG. 2 depicts a personal cooler/heater device 10 worn about the neck of a user, the user shown drawn in phantom lines. If desired, device 10 may be worn in headband fashion around the forehead of a user, as shown in phantom. It will be appreciated from the configuration shown that device 10 may be worn over other parts of the body as well, e.g., a thigh, shoulder.

Device 10 preferably includes a generally "C"-shaped housing 20 that preferably encircles at least 180° and provides an opening 30 sized to permit housing 20 to pass around the neck 40 (or other body portion) of a user. In the preferred embodiment, housing 20 is formed of a plastic material (e.g., ABS plastic) and retains a thermally conductive heat sink-heat dissipator member 50. In such embodiment, member 50 is a thin (e.g., 1 mm to perhaps 2 mm) perhaps 28 cm length of thermally conductive material, e.g., stainless steel or aluminum metal. Collectively, housing 20 and member 50 are sufficiently resilient to fit snugly but comformally and comfortably around a substantial portion of the user's neck.

The user-facing surface 52 of member 50 is urged into contact with the portion of the user's body portion to be temperature regulated. Understandably, a device 10 intended for forehead or thigh use will be sized to fit comfortably about these body parts. If desired, housing 20 could encompass less than about 180° but could be attached around the body portion to be temperature regulated using straps 55 or the like. The free end of such straps could be snapped together, or could be attached using regions of mating Velcro™ brand material, or the like.

As will be described, device 10 has at least one air intake port or vent 60 and at least one air exhaust port or vent 70. Incoming air, denoted by large arrows labelled "IN", can enter device 10 via port(s) 60, and exhaust or outgoing air, denoted by large arrows labelled "OUT" exits device 10 via port(s) 70 If desired, a single port may be used for both intake and exhaust purposes. FIG. 2 does not depict a screen that preferably covers output port(s) 70, primarily to prevent a user from inserting a finger into the internal mechanism (which preferably includes a rotating fan blade).

Figure 3:
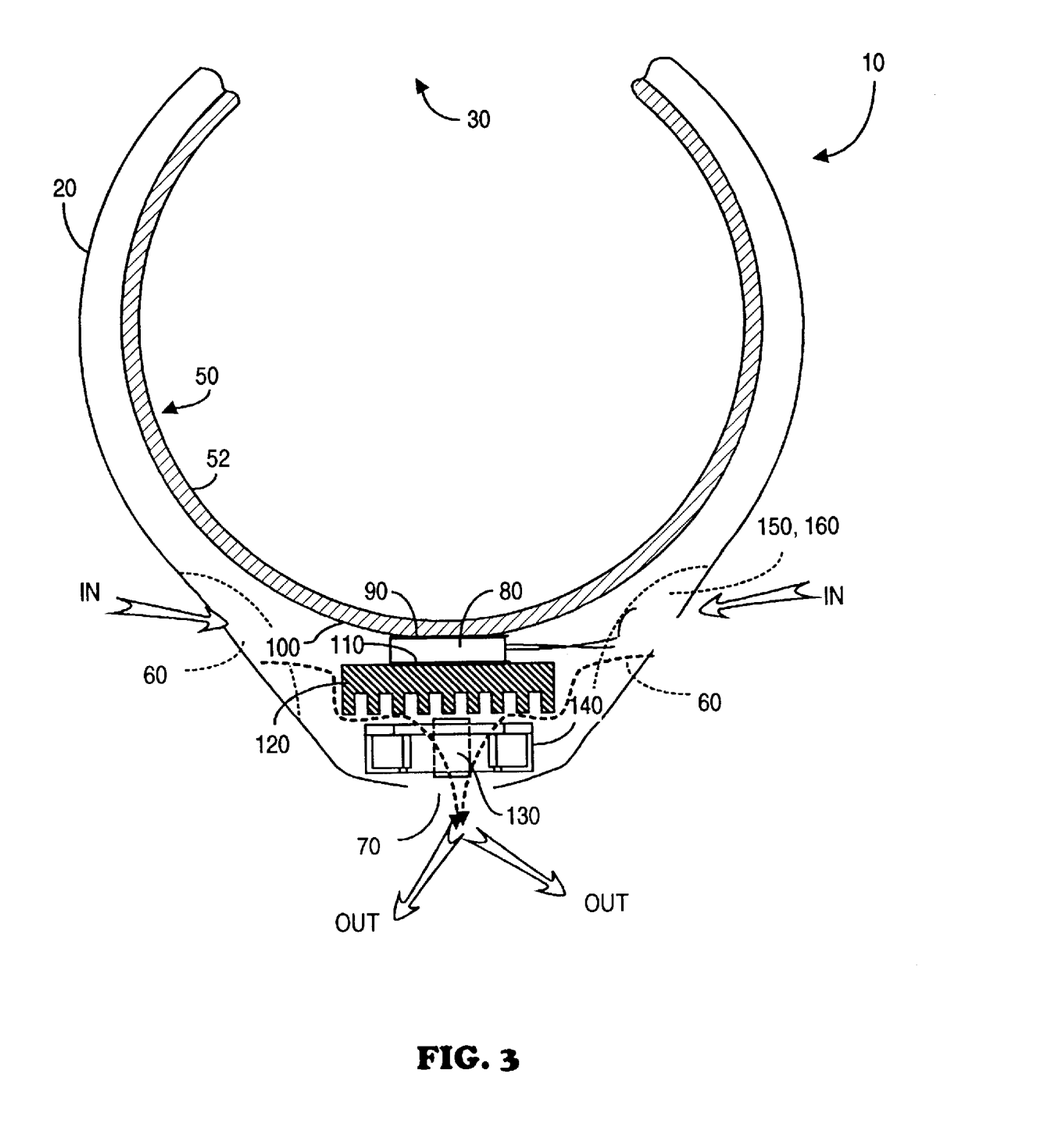
FIG. 3 is a cross-sectional view of the present invention.

As best seen in FIG. 3, a commercially available Peltier thermo-voltaic ("T-V") module 80 is retained within housing 20. Such T-V modules are available from manufacturers such as Materials Electronic Products Corp. of Trenton, N.J., manufacturers of the Melcor lines of modules. T-V module 80 has a user-facing surface 90 that is in intimate thermal contact with the non-user-facing surface (e.g., back surface) 100 of dissipator member 50. This interface is such that good thermal transfer occurs between surfaces 90 and 100. Preferably commercially available thermal grease such as is commonly used to improve heatsinking of transistors and the like is used at this interface to improve thermal transfer.

T-V module 80 has an opposite surface 110 (e.g., back surface) to which a preferably finned heat sink 120 is well coupled thermally to encourage good heat transfer. Again, use of a commercially available thermal grease is used at the interface between heatsink 120 and back surface 110. If desired, rear surface 110 of T-V module 80 could be fabricated to define a large rear surface area (relative to the front area of surface 90) to promote good heat transfer to or from surface 110, thus eliminating the need for a separate heatsink. Such increase in surface can be achieved by etching, forming grooves or micro-grooves, sand blasting, among other techniques.

Preferably a small fan 130 and fan blade assembly 140 is disposed within housing 20, along with a battery pack 150 (also denoted B1). Fan 130 preferably can develop perhaps 3000 RPM when coupled to a drive voltage of a few volts. In contrast to many prior art devices, the present invention is functional without a fan. However the inclusion of a fan promotes heat transfer and thus thermal efficiency of the present invention. A battery pack 150 powers T-V module 80, fan 130, and control electronics 160. The fan and blade promote heat transfer from heat sink 120 to the ambient air. Ambient air enters housing 50 via port(s) 60 (e.g., "IN") and exits housing 50 via port(s). As will be described, one or more air vents 130 facilitates transfer of ambient air into device 10 or exhaust of air of air from device 10. Housing 10 also provides user controls 170.

Figure 4A:
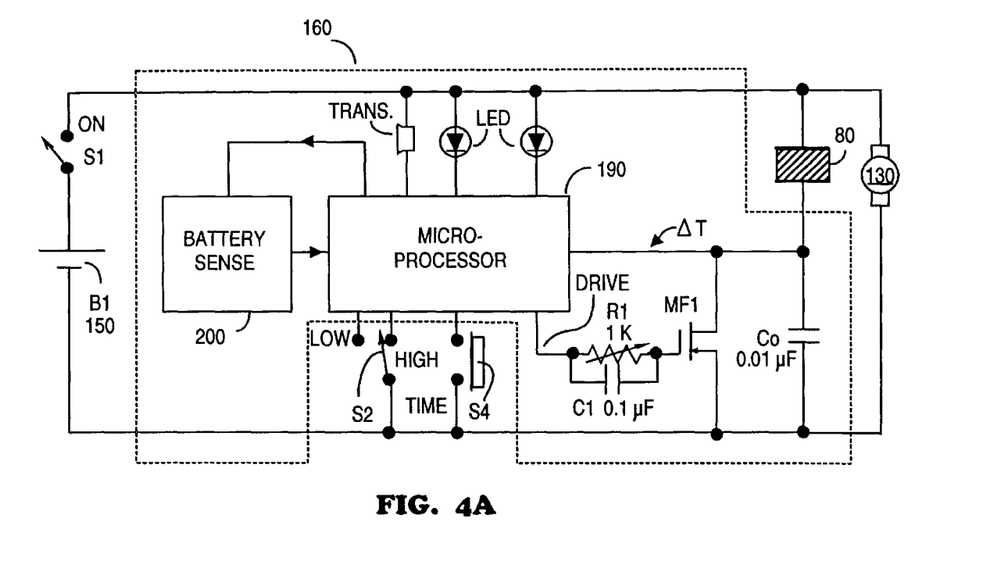
FIG. 4A is a functional block diagram of the present invention.
Figure 4B:
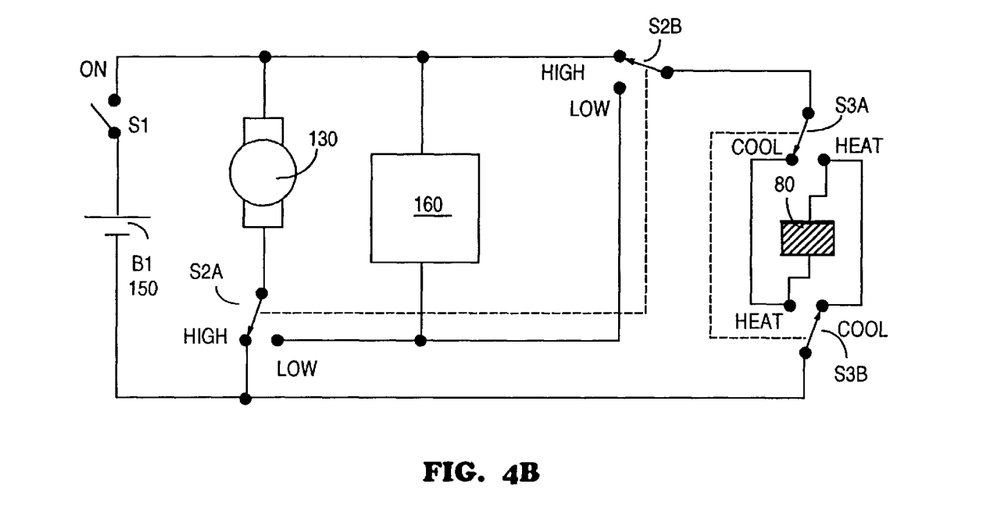
FIG. 4B is a block diagram of a first implementation of a high/low power embodiment of the present invention.

Referring to FIGS. 4A and 4B, exemplary such controls 170 can include an on-off switch S1, a high/low heating or cooling effect switch S2, and cool or heat mode switch S3, a thermostat control (e.g., R1), and a timer control S4. Although intended to be DC powered from internal batteries 150, if desired an external power source (not shown) can be used and power can be coupled to device 10 via a preferably removable power cable 180.

Among other functions, electronics 140 responds to user selections made with controls 170 to cause surface 70 of module 60 to sink heat (e.g., cooling mode) or to source heat (e.g., heating mode). As shown in FIG. 4A, preferably electronics 140 includes a microprocessor 190 (e.g., an 8-bit unit such as the PIC 12CO0), a battery sense circuit 200 that can alert the user via light emitting diodes ("LEDs") and/or audio signal (via a sound transducer "TRANS"), when the voltage of the power source B1 (or 150) is becoming too low to sustain operation of device 10, and thermostat feedback control elements MF1, R1, Co, C1. Electronics 140 is coupled to receive polarized power from supply B1 (or 150) vis on/off switch S1, and to provide power of the desired polarity or bias orientation to Peltier module 80. Electronics 140 preferably also is coupled to control elements such as a high/low power switch S2, timer control switch S3, heat/cool mode selection switch S4 (see FIG. 3B) and a time control S4.

In the cooling mode, device 10 will sink and carry away heat, thus cooling the user. In cooling mode, electronics 140 biases Peltier module 80 appropriately, and causes fan 110 to move air away from heat sink 100, thus cooling surface 90, which in turn causes user-facing surface 70 to become even cooler. As a result, member 50 is cooled, and the portions of the user's body in contact with the user-facing surface 52 member 50 are cooled. As will be described, electronics 140 also serves to ensure that user-facing surface 70 does not become too cold.

In the heating mode, device 10 will generate heat at user-facing surface 70, thus warming member 60 and portions of the user's body in contact with member 50. In heating mode, electronics 140 reverses bias on Peltier module 50 (relative to cooling mode), and fan 110 carries away heated air from heat sink 100, which causes userfacing surface 70 to become even warmer. Electronics 140 also serves to ensure that user-facing surface 70 does not become too warm. In FIG. 4A, change of mode from cooling to heating may be effected by reversing the connections to the two leads of module 80.

Although fan 110 might be powered by other than a battery (e.g., solar cells, mechanical wind-up mechanism, Peltier thermo-voltaic module 50 requires electrical energy for operation in the present invention.

Figure 4C:
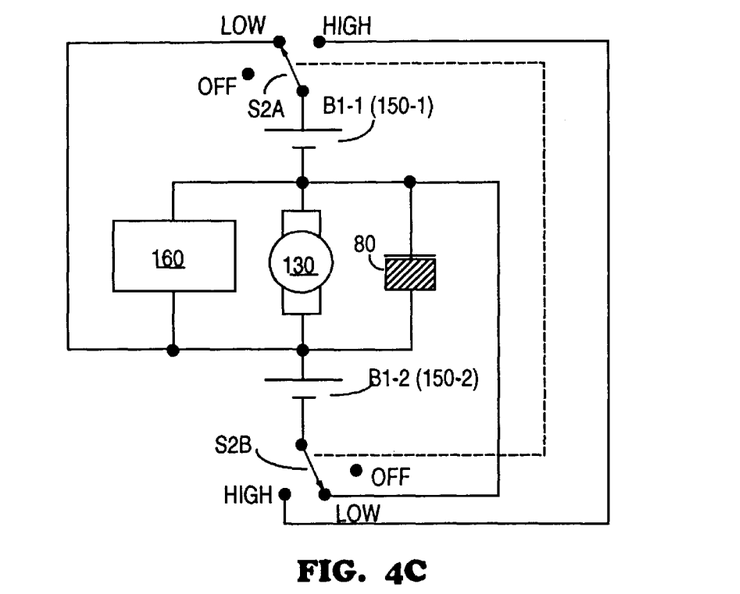
FIG. 4C is a block diagram of a second implementation of a high/low power embodiment of the present invention.

Operation of the various embodiments shown in FIGS. 4A–4C will now be described in detail. In FIG. 4A, power source B1 (or 150) is coupled via on/off switch S1 to control circuit 160. Circuit 160 preferably includes microprocessor 190, a battery sense unit 200, a drive device MF1 (and associated drive components, here resistor R1 and capacitor C1), as well as a discharge capacitor Co. Also coupled to circuit 160 is Peltier thermovoltaic module 80 and fan unit 130.

Responsive to settings of various controls including, here, switch S2, microprocessor 190 outputs a drive signal (denoted "DRIVE") to the control lead of drive device MF1. In the preferred embodiment, MF1 is a MOS transistor, and the control lead is its gate lead. Feedback components R1 and C1 are coupled in series between the gate lead of MF1 and the output drive port of microprocessor 190. The output signal at device MF1 (e.g., drain lead) is denoted ΔT.

When the drive signal ("DRIVE") at the output drive port of microprocessor 190 turns MF1 on, the lower terminal of Peltier thermo-voltaic module 80 is close to ground potential (for the configuration shown). So biased, a maximum heating or cooling effect (depending upon bias polarity) from module 80 will occur. Fan 130 preferably is operated only when on/off switch S1 is closed. Optional switch S2 enables the user to select relatively high or low heating or cooling effect (depending upon whether device 10 is used in heating or cooling mode). In the preferred embodiment, the amplitude of the DRIVE signal remains substantially constant but duty cycle is varied, for example from perhaps 50% to perhaps 99% to vary low versus high operation mode of module 80. Of course a combination of variation in duty cycle and amplitude of the drive signal could be used, as could other modulation modes to vary duty cycle of module 80. Thus, depending upon the position of power switch S2, microprocessor 190 will nominally operate in one of two preselected two cycle modes, e.g., low power or high power.

Optional switch S4 permits the user to automatically operate device 10 for a predetermined time, say ten minutes, after which the device turns itself off. This is a useful feature, especially when the user's hands and/or attention are otherwise occupied. If desired, various pins on microprocessor 190 could be coupled to a switch to give the user options as to the length of the predetermined time that is activated using switch S4.

FIG. 4B depicts one method by which high and low mode operation may be user-selected, as well as a mechanism for changing from heating to cooling mode, or vice versa. As shown in FIG. 4B, in high mode, both Peltier module 80 and motor 130 are coupled in parallel across B1. As such, each sees the full potential of B1, e.g., 3 VDC from a pair of D cells. In high mode, perhaps 600 mA of current will be drawn by the load comprising module 80 and motor 130 (plus a relatively small amount of current for electronics 160). Assuming the D cells are rated at 10 AHr, battery lifetime may approach 20 hours. Note that even in high mode, module 80 operates with surprisingly high efficiency (perhaps 30%), at low voltage (e.g., 3 VDC) and low current (600 mA). This low voltage, low current operation mode is in contrast to prior art biasing of modules such as module 80.

In low power mode, double-gang switch S2A–S2B causes the Peltier device and the motor to be connected in series with each other, and the series connection to be coupled across B1. In this mode, the Peltier device sees only the fraction of the voltage from B1 that is not dropped (due to ohmic current×resistance drop) across the motor. In low mode operation, total current drawn by the motor, the Peltier module and the electronic circuitry will be about 150 mA. Battery lifetime should reasonably be two or three times that of the high power mode configuration.

In FIG. 4B, double gang switch S3A–S3B reverses polarity of whatever voltage from B1 is to be seen by the Peltier device, to change heating/cooling mode. FIG. 4C depicts another configuration whereby power mode and heating/cooling mode may be user-controlled. Of course other methods of varying coupling of source of operating potential (B1 or 150) to the present invention may be used.

Figure 5A:
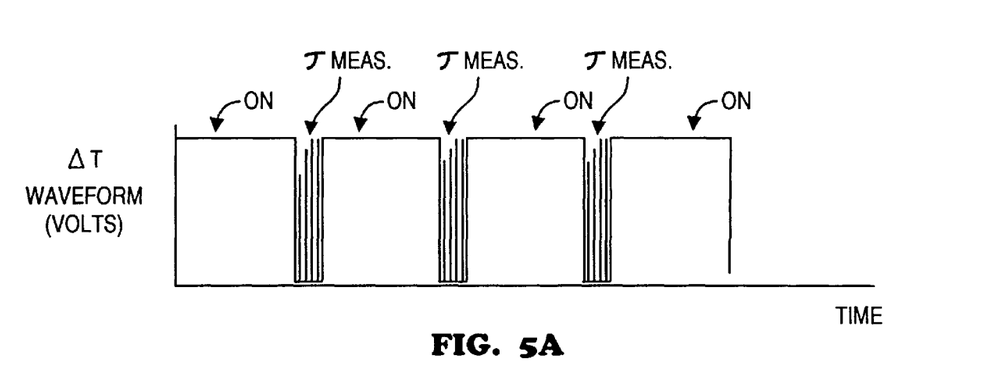
FIGS. 5A and 5B are waveforms depicting module temperature sense-feedback signals, according to the present invention.
Figure 5B:
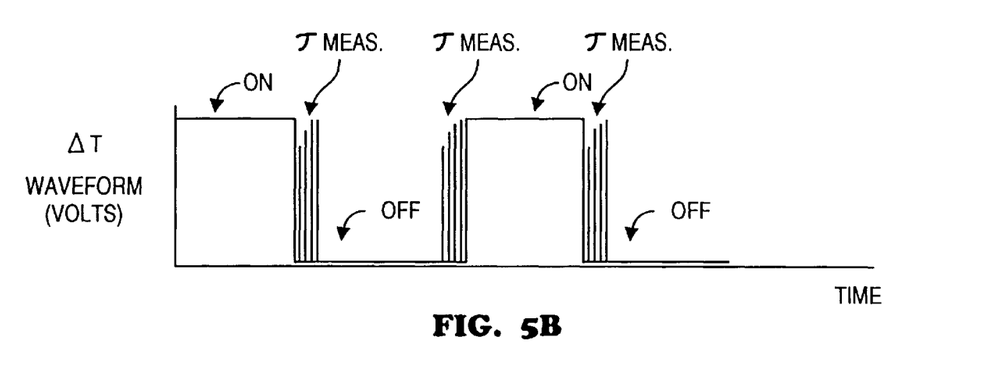

FIGS. 5A and 5B provide insight as to the use of feedback to fine tune temperature control of the present invention. The $\Delta T$ waveforms noted in FIGS. 5A and 5B are measured across module 80. In the "on" portion of the duty cycle, device MF1 is biased on by the DRIVE output from microprocessor 190. In the embodiment of FIG. 4A, for example, essentially the full potential of B1 will appear across module 80. During the "off" portion of the duty cycle, MF1 is biased off, and the $\Delta T$ waveform voltage across capacitor Co will be discharged toward ground via drain-to-source of MOS device MF1. (It is understood that devices other than a MOS device may be used to control voltage seen by module 80.)

With no external bias applied to module 80 (e.g., from circuit 160), module 80 will output a voltage as a function of the temperature differential across the two surfaces or plates of the module. Microprocessor 190 can create this no external bias condition by turning-on transistor MF1 to fully discharge capacitor Co, after which MF1 is turned-off. With no bias applied, the potential across capacitor Co will begin to increase (see FIGS. 5A and 5B) and is measured. The measured no-bias voltage ($\Delta T$), corresponding to heat differential across module 80 in the absence of electrical current, is then fedback to microprocessor 190. Microprocessor 190 preferably can access a look-up table or other database correlating no-bias voltage ($\Delta T$) versus module temperature differential. Such database may be stored in memory associated with the microprocessor or in memory external to the microprocessor integrated circuit. If measurement of the fed-back no-bias voltage indicates too small a temperature differential across module 80, microprocessor 190 is commanded to increase duty cycle (and/or amplitude) of the DRIVE signal.

It is not necessary to constantly monitor the no-bias voltage developed by module 80. In FIGS. 5A and 5B, the duration of the no-bias voltage readings is denoted $\tau$-MEAS. (for $\tau$-MEASUREMENT). It can suffice for CPU 190 to enter a measurement mode every thirty seconds or so, and to take samples for a few seconds. It is seen in FIG. 5B that there will be an exponential envelope to the $\tau$-measurements. This envelope results from the R-C time constant associated with capacitor Co and the effective shunt resistance it sees.

An additional advantage of the pulsed operation of Peltier thermo-voltaic module 80 is that the reverse cooling or heating effect may be minimized when device 10 is powered off. In the preferred embodiment, the basic pulse frequency of waveforms such as shown in FIGS. 5A or 5B nominally lies within a range of perhaps 5 Hz to perhaps 200 Hz, although lower or higher frequency limits may be used. Duty cycle of the pulsed waveform may be in the range of perhaps 2% to perhaps 95%, although lower or higher duty cycles may be used.

The present invention can advantageously reduce the reverse-effect noted when turning-off a prior art Peltier-module type device. During power turn-off, the present invention can gradually (rather than instantly) reduce duty cycle from its present value down to zero. As a result the present invention is cycled off gradually, over a time duration of perhaps a minute or more, in a cycle-down operation that can be executed transparently to the user. Assume that a user wishes to turns-off the present invention using switch S1. Microprocessor 190 can be configured to intercept the S1 turn-off and to command transistor MF1 to achieve a gradual reduction in operational duty cycle until the Peltier module is in fact off. Understandably in this configuration, operating potential continues to be received by the microprocessor even when S1 is off.

Thus, if device 10 has been used in a heat generating mode to warm the user, turning-off device 10 will not tend to instantly cool inner surface 52 of heat dissipating member 50. Similarly, if device 10 has been used to cool the user, turning-off operating power will not instantly cause inner surface 52 of member 50 to try to warm the user.

Fan blade assembly 140 may be implemented in a variety of manners. Assembly 140 may be propeller-like in configuration, or may include radially configured blades, or axially configured blades, or even a combination of such blade types. It is understood that the function of fan 130 and blade assembly 140 is to remove heat from back surface 110 of module 80. With efficient heat removal, user-facing surface 90 of module 80 can more effectively change the temperature of surface 52 of member 50, and thus of the user body that is contacted by surface 52.

From the foregoing description, it is seen that the present invention provides a self-contained, light weight device that may be operated from self-contained batteries to controllably heat or cool a portion of a user's body. The device operates dry in that no cooling liquid is required, in contrast to prior art devices. Mechanically, the device may be implemented in a straightforward fashion, without requiring fabrication of intricate mechanical parts, again in contrast to the prior art, including cooling-only devices such as provided by the Strauss patent. The present invention requires little or no maintenance, other than replacing or recharging the power supply as necessary. It is understood that power supply B1 may comprise ordinary alkaline batteries, or rechargeable batteries, including without limitation NiCd, Li ion, and NiH.

As noted in FIG. 4A, optionally indicators such as a LED or a sound transducer "TRANS" may be provided to advise the user as to the state of the battery power supply B1. For example, an LED may be commanded by the microprocessor to flash red to signify lower battery condition, e.g., perhaps less than 15 minutes of operation of device 10 is remaining, after which device 10 will self-cycle off. If the battery is in good condition, the same (or another) LED may flash green, to indicate a timing cycle. A steady green LED signal may signify that device 10 is on in normal operational mode. In addition to or instead of visual indicator(s), an audio indicator such as a transducer may be used to signal the different states of the battery, and operational modes.

Modifications and variations may be made to the disclosed embodiments without departing from the subject and spirit of the invention as defined by the following claims.

What is claimed is:

1. A self-contained dry-operating device to thermally alter external temperature of a portion of a user's body, comprising:
   a heat dissipating member having a user-facing surface and an opposite rear surface, said member adapted to urgingly contact said portion of said user's body;
   a Peltier thermo-voltaic module, having a first surface spaced-apart from a second surface, disposed such that said first surface is in thermal contact with a portion of said rear surface of said member;
   means for coupling a source of polarized electrical energy to energize said module;
   wherein when said means for coupling energizes said module with a first bias polarity said module reduces temperature of said rear surface to cool said user; and when said means for coupling energizes said module with a second bias polarity said module increases temperature of said rear surface to warm said user; and
   a control unit coupled to provide said module with a pulsed drive signal defining module-on and module-off times, said control unit including means for sensing a bias potential across said module during at least some said module-off times and for feeding back sensed said bias potential to temperature control operation of said module.

2. The device of claim 1, further including at least one of (a) said module has a second surface (of said module has having greater surface area than said first surface, and (b) said module has a second surface in good thermal contact with a heat sink.

3. The device of claim 1, further including a fan unit disposed to move ambient air across at least a portion of said module that faces away from said heat dissipating member.

4. The device of claim 3, further including a device housing;
   said housing retaining at least one of (a) said heat dissipating member, (b) said fan unit, and (c) said source of polarized electrical energy comprising a battery.

5. The device of claim 1, wherein said control unit includes a switch enabling a user of said device to switch between heating mode and cooling mode.

6. The device of claim 1, wherein said heat dissipating member generally defines a "C" shape sized to contact said portion of said user's body.

7. The device of claim 1, wherein said control unit includes at least one of (a) a central processor unit, and (b) means for minimizing reverse-bias operation of said module when said operating potential to said module is turned off.

8. The device of claim 1, wherein said control unit includes a central processor unit (CPU), coupleable to said source of polarized electrical energy and to said module, controlling at least one characteristic of said pulsed drive signal selected from a group consisting of (a) duty cycle of said signal, and (b) amplitude of said signal.

9. The device of claim 1, wherein said device includes at least one of (a) a component permitting user-selection of heating mode or cooling mode operation of said device, (b) a component permitting user control over temperature of said user-facing surface of said heat dissipating member, and (c) a component enabling user-selection of high versus low operating mode of said device.

10. The device of claim 1, wherein said control unit includes a control permitting user regulation of temperature at said first surface within about 1° C.

11. The device of claim 1, further including a component to signal low energization level of said source of polarized electrical energy.

12. The device of claim 14, further including a component enabling energization of said device for a predetermined time.

13. The device of claim 14, further including a control unit permitting user regulation of temperature at said first surface within about 1° C.

14. A self-contained dry-operating device to thermally alter external temperature of a portion of a user's body, comprising:
   a device housing;
   a heat dissipating member having a user-facing surface and an opposite rear surface, said member adapted to urgingly contact said portion of said user's body and said member having at least a portion of said opposite rear surface retained in said housing;
   a Peltier thermo-voltaic module, retained in said housing and having a first surface spaced-apart from a second surface, disposed such that said first surface is in thermal contact with a portion of said rear surface of said member;
   means for coupling a source of polarized electrical energy to energize said module with a pulse train signal defining module-on times and module-off times, said means for coupling being retained in said housing; and
   at least one component selected from a group consisting of (a) a component to signal low energization level of said source, (b) a component permitting user-selection of heating mode or cooling mode operation of said device, and (c) a component permitting user control over temperature of said user-facing surface of said heat dissipating member, and (d) a component enabling user-selection of high energy versus low energy operation of said device;
   wherein when said means for coupling energizes said module with a first bias polarity said module reduces temperature of said rear surface to cool said user; and when said means for coupling energizes said module with a second bias polarity said module increases temperature of said rear surface to warm said user.

15. The device of claim 14, wherein said source of polarized electrical energy includes a battery power supply, retained by said housing.

16. The device of claim 14, further including a central processor unit (CPU), coupleable to said source of polarized electrical energy and to said module, controlling at least one characteristic of said pulse train signal selected from a group consisting of (a) duty cycle of said signal, and (b) amplitude of said signal.

17. The device of claim 14, further including means for sensing a bias potential across said module during at least a portion of said module-off times and for feeding back sensed said bias potential to temperature control operation of said module.

18. The device of claim 14, further including a fan disposed to remove heat from said second surface of said module.

19. A method of altering external temperature of a portion of a user's body with a self-contained dry-operating device, comprising the following steps:

(a) disposing a heat dissipating member having a user-facing surface and an opposite rear surface so as to urgingly contact said portion of said user's body with said user-facing surface;

(b) thermally coupling a Peltier thermo-voltaic module having a first module surface in good thermal contact with a portion of said rear surface of said member;

(c) selectively coupling a source of polarized electrical energy to energize said module with a pulsed drive signal such that when said module is energized with a first bias polarity said module reduces temperature of said rear surface to cool said user; and when said module is energized with a second bias polarity said module increases temperature of said rear surface to warm said user: and (d) sensing bias potential across said module during a portion of time said pulsed drive signal is off and feeding back sensed said bias potential to temperature control operation of said module.

20. The method of claim 19, further including providing user control over at least one device function selected from a group consisting of (a) user-selection of heating mode or cooling mode operation of said device, (b) user control over temperature of said user-facing surface of said heat dissipating member, and (c) a component enabling user-selection of high energy versus low energy operation of said device.

* * * * *

UNITED STATES PATENT AND TRADEMARK OFFICE
CERTIFICATE OF CORRECTION

PATENT NO. : 6,125,636
DATED : October 3, 2000
INVENTOR(S) : Charles E. Taylor, et al.

It is certified that error appears in the above-identified patent and that said Letters Patent is hereby corrected as shown below:

<u>Column 9, claim 2,</u>
Line 56, delete "(of said module has".

Signed and Sealed this

Twenty-third Day of October, 2001

Attest:

NICHOLAS P. GODICI
Attesting Officer    Acting Director of the United States Patent and Trademark Office